United States Patent [19]

Ausich et al.

[11] Patent Number: 5,648,564
[45] Date of Patent: Jul. 15, 1997

[54] PROCESS FOR THE FORMATION, ISOLATION AND PURIFICATION OF COMESTIBLE XANTHOPHYLL CRYSTALS FROM PLANTS

[75] Inventors: Rodney L. Ausich; David J. Sanders, both of Des Moines, Iowa

[73] Assignee: Kemin Industries, Inc., Des Moines, Iowa

[21] Appl. No.: 576,778

[22] Filed: Dec. 21, 1995

[51] Int. Cl.$^6$ .................................................. C07C 35/08
[52] U.S. Cl. ..................... 568/834; 568/832; 568/822; 568/825; 568/913
[58] Field of Search ................................. 568/834, 832, 568/822, 825, 913

[56] References Cited

U.S. PATENT DOCUMENTS 4,048,203  9/1977  Philip .
5,382,714  1/1995  Khachik .

OTHER PUBLICATIONS

Tyczkowski and Hamilton, *Poultry Sci.*, 70(3): 651–654, (1991).
Strain, H., *Leaf Xanthophylls*, Carnegie Institution, Washington, D.C. (1936).
J. Food Sci. (1976), 41(1), 163–4. 1976.

*Primary Examiner*—Gary Geist
*Assistant Examiner*—Karl Puttlitz
*Attorney, Agent, or Firm*—Welsh & Katz, Ltd.

[57] ABSTRACT

A process for forming, isolating and purifying xanthophyll crystals, preferably lutein from marigold flower petals, zeaxanthin from wolfberries or capsanthin and capsorubin from red pepper, is disclosed. A xanthophyll diester-containing plant extract is saponified in a composition of propylene glycol and aqueous alkali to form xanthophyll crystals. Crystallization is achieved without the use of added organic solvents. The crystals are isolated and purified. The substantially pure xanthophyll crystals so obtained are suitable for human consumption and can be used as a nutritional supplement and as an additive in food.

8 Claims, No Drawings

PROCESS FOR THE FORMATION, ISOLATION AND PURIFICATION OF COMESTIBLE XANTHOPHYLL CRYSTALS FROM PLANTS

TECHNICAL FIELD

The present invention relates to a process for forming, isolating and purifying carotenoid compounds, and more particularly to a process for forming, isolating and purifying plant-produced xanthophyll compounds in a crystalline form suitable for human consumption.

BACKGROUND OF THE INVENTION

Carotenoids include hydrocarbons (carotenes) and their oxygenated, alcoholic, derivatives (xanthophylls). Representative examples of carotenes include beta-carotene, alpha-carotene, and lycopene. Representative examples of xanthophylls include lutein, zeaxanthin, capsorubin, capsanthin, astaxanthin, and canthaxanthin.

Carotenoids are abundant in fruits and vegetables and have been studied extensively as antioxidants for the prevention of cancer and other human diseases. Among the dietary carotenoids, the focus has been on beta-carotene that has been established to play an important role in the prevention of various types of cancer.

More recent research has shown that other carotenoids, particularly the xanthophylls, posses strong antioxidant capabilities and may be useful in the prevention of diseases including cancer. For example, it has been reported that the consumption of lutein and zeaxanthin leads to a 40 percent reduction in age-related macular degeneration (Seddon et al., 1994, *J. Amer. Med. Assoc.* 272 (18): 1413–1420). It has also been reported that an increased level of serum carotenoids other than beta-carotene is associated with a lower incidence of heart disease (Morris et al., 1994, *J. Amer. Med. Assoc.* 272 (18): 1439–1441). The xanthophylls, because of their yellow to red coloration and natural occurrence in human foods, also find uses as food colorants. Thus there is an increasing need for substantially pure xanthophylls, which can be used as nutritional supplements and food additives.

Although present in many plant tissues, carotenoids free of other plant pigments are most readily obtained from flowers (marigold), fruits (berries) and root tissue (carrots and yellow potatoes). The hydrocarbon carotenes are typically present in uncombined, free from in chromoplast bodies within plant cells. Xanthophylls are typically present in plant chromoplasts as long chain fatty esters, typically diesters, of acids such as palmitic and myristic acids.

Although chemical processes for the synthesis of xanthophylls from commercially available starting materials are known, such processes are extremely time-consuming, involve multiple steps, and have not provided an economical process for the production of xanthophylls. A more economical route for the large-scale production of substantially pure xanthophylls is a process that extracts, isolates and purifies xanthophylls from natural sources. However, previous methods that isolate xanthophylls from plants use a number of organic solvents.

Previous investigators have also used a commercially available saponified marigold oleoresin, which contained free lutein, as a starting material, and then added the appropriate solvents to crystallize lutein from the saponified oleoresin (Tcyczkowski and Hamilton, *Poultry Sci.* 70 (3): 651–654, 1991; U.S. Pat. No. 5,382,714). The preparation of purified lutein difatty acid esters is also described in U.S. Pat. No. 4,048,203.

Methods for obtaining leaf xanthophylls are described in H. Strain, *Leaf Xanthophylls*, Carnegie institution, Washington, D.C. (1936). Among the techniques described, including those for obtaining xanthophylls occurring free in the leaves, Strain describes obtaining free xanthophylls from xanthophyll diesters present in the pods (calyx) of *Physalis alkekengi*.

In that latter preparation, at pages 99–104, the almost dried pods were cut into small sections with a meat grinder, and the pieces extracted with petroleum ether. The extract was concentrated to a small volume and the xanthophyll esters present were saponified with alcoholic potash. The alcohol was unnamed, but is presumed to be methanol from the preceding text. Water was added to the alcoholic solution to precipitate the xanthophylls. The precipitated xanthophylls were then crystallized several times from chloroform and a co-solvent such as methanol or petroleum ether, and then from pyridine.

The above procedure described by Strain has several disadvantages in producing a comestible xanthophyll. First, the hydrophobic petroleum ether used to extract the xanthophyll diesters is not removed prior to saponification and can be entrapped in the precipitated, hydrophobic xanthophylls. Second, use of a monohydric alcohol such as methanol or even ethanol can cause formation of water-insoluble fatty acid methyl or ethyl esters that can also be entrapped with the hydrophobic xanthophylls. Such entrapment may be the reason that so many recrystallization steps were required. Very cold temperatures such as −12° C. and −70° C. were also required for those recrystallizations.

The disadvantage of these methods is that the xanthophylls can retain some of the solvent(s) from which they are isolated and purified. In addition, these methods require the washing of the xanthophylls with more solvents. The solvents can be usually removed by drying the crystals at elevated temperatures. But in some instances, the solvent is difficult or impossible to remove. Traces of toxic organic solvents in the isolated, purified xanthophyll product make it unsuitable for human consumption. Another disadvantage of the use of a process that employs organic solvents is that such solvents are difficult to handle and present physical and chemical hazards. Still another disadvantage of that use is that organic solvents are a hazardous waste and present a disposal problem.

There is therefore a need for an economical means of production of an edible or comestible, substantially pure xanthophyll such as lutein or zeaxanthin in which the use of toxic or hazardous organic solvents is not employed. The process disclosed herein after provides such a comestible xanthophyll.

BRIEF SUMMARY OF THE INVENTION

The present invention relates to a process for extracting, isolating and purifying xanthophylls, preferably lutein or zeaxanthin, from a xanthophyll diester-containing plant extract. The plants are preferably those known to contain high concentrations of the desired xanthophyll diester such as lutein in marigold flowers (*Tagetes sp.* such as *Tagetes erecta*), zeaxanthin in the wolfberry (a *Lycium sp.* such as *Lycium barbarum*) or capsanthin and capsorubin, in the pepper plant (a *Capsium sp.* such as *Capsicum annum*). The process contemplates use of a xanthophyll diester-containing food grade plant extract (oleoresin) that is free of organic solvent; i.e., the oleoresin contains less than 1 percent organic solvent. The extract is admixed with a composition containing propylene glycol and an aqueous alkali, preferably potassium hydroxide, to form a reaction mixture of which oleoresin and propylene glycol together constitute at least 75 weight percent. The reaction mixture so formed is maintained at a temperature of about 65° C. to about 80° C. for a time period (typically at least 3 hours) sufficient to saponify the xanthophyll diester and form a saponified reaction mixture that contains free xanthophyll in the form of crystals. The saponified extract is admixed with a diluting amount of water to dissolve the water-soluble impurities and reduce the viscosity of the reaction mixture. The diluted admixture is gently admixed until homogeneous and then filtered to collect the xanthophyll crystals. The collected xanthophyll crystals are washed with warm water, and dried. No organic solvent other than propylene glycol is used in the isolation and purification of the xanthophyll from the xanthophyll diester-containing oleoresin.

The present invention has several advantages. One advantage of this invention is that it provides a process for producing a substantially pure xanthophyll that is suitable for human consumption without the use of relatively toxic organic solvents during isolation or crystallization. Another advantage of this invention is that it provides a process for producing a comestible, substantially pure xanthophyll without the need for recrystallization. Yet another advantage of this invention is that it provides a process for producing a comestible, substantially pure xanthophyll that is economical and easy to perform on a large commercial scale. Still further advantages will be apparent to a worker of ordinary skill from the description that follows.

DETAILED DESCRIPTION OF THE INVENTION

According to the present invention, a xanthophyll, preferably lutein, zeaxanthin or capsanthin and capsorubin is formed, isolated and purified from xanthophyll diester-containing plant matter, preferably a plant known to contain high concentrations of the desired xanthophyll diester. Marigold flowers (*Tagetes erecta*) are an excellent source of lutein because they contain one of the highest known concentrations of lutein diesters in nature, whereas the wolfberry fruit (*Lycium barbarum*) is an excellent source of zeaxanthin because it contains high concentrations of zeaxanthin diesters, and the pepper plant (*Capsicum annum*) is a good source of capsanthin and capsorubin because of the high concentration of capsanthin and capsorubin diesters therein. Other plants that are known to contain high concentrations of desired xanthophylls can also be utilized.

A contemplated plant source contains the xanthophyll in the esterified form as a mono- or di-$C_{12}$-$C_{18}$ long chain, fatty acid such as lauric, myristic, oleic, linolenic and palmitic acids. Lutein in marigold flowers, zeaxanthin in wolfberries and capsanthin and capsorubin in pepper plants are present as xanthophyll diesters. The free or non-esterified xanthophyll can be found in other plants such as spinach, broccoli, kale and corn.

The xanthophyll esters are extracted from the plant, preferably from the flower, fruit or root, with an appropriate organic solvent or a mixture of solvents that are themselves readily removable from the extract. The use of flowers, roots and fruits as a source of a desired xanthophyll avoids difficulty in the separation of the xanthophylls from other pigments such as chlorophyll.

In one embodiment of the invention, commercially available dried and ground marigold flowers (*Tagetes erecta*) are used as a source of lutein. In another embodiment, wolfberry fruits (*Lycium barbarum*) are used as a source of zeaxanthin, whereas red peppers (*Capsicum annum*) are a source of capsanthin and capsorubin.

Organic solvents that have been used to extract carotenoids from plants include methanol, acetone, ethyl acetate, diethyl ether, petroleum ether, hexanes, heptanes, chloroform, and tetrahydrofuran. In one illustrative embodiment of the invention, lutein diester is extracted from dried marigold flowers with hexane. In another illustrative embodiment, zeaxanthin diester is extracted from dried wolfberries with hexane and ethyl acetate. The extraction is carried out according to procedures known in the art. The solvent(s) is removed, resulting in an extract that contains a high level of the xanthophyll esters and is about 99 percent and preferably about 99.9 percent free of the extracting organic solvent; i.e., contains less than about 1 percent and preferably less than about 0.1 percent organic solvent by weight. The resulting solvent-free extract is referred to in the art as an oleoresin.

Exemplary toxicities of propylene glycol and several solvents previously used for xanthophyll crystal recovery are available from several sources. Comparative oral toxicities in the rat from *The Merck Index*, 11th ed., Merck & Co., Inc., Rahway, N.J. (1989) are provided in the Table below as $LD_{50}$ values.

| Reported Rat Toxicities | |
|---|---|
| Solvent | $LD_{50}$ ml/kg |
| Propylene Glycol | 25 |
| Ethyl Acetate | 11.3 |
| Ethyl Alcohol | 10.6–7.6 |
| Chloroform | 2.18 |
| Pyridine | 1.58 |

In the present invention, the oleoresin so formed is saponified by admixture with propylene glycol (1,2-propanediol) and an aqueous alkali, preferably potassium hydroxide. It was surprisingly discovered that the free xanthophylls formed in the aqueous propylene glycol-containing saponified oleoresin were present as crystals. The crystals were clearly visible under a microscope. Thus, crystallization of the xanthophylls was achieved directly via the saponification reaction and not by the addition of various organic solvents as has been done previously. Also, unlike previous methods that used saponified marigold oleoresin as a starting material to isolate lutein (Tcyczkowski and Hamilton, *Poultry Sci.* 70 (3): 651–654, 1991; U.S. Pat. No. 5,382,714), there was no need to crystallize lutein from the saponified marigold oleoresin by the addition of organic solvents.

Large crystal size is important to obtaining xanthophyll at the purity desired. To obtain the desired large crystals (average size about 0.01 to about 0.1 mm) the concentrations of the four constituents of the saponification reaction mixture are preferably present at about 35 to about 50 weight percent oleoresin to about 30 to about 45 weight percent propylene glycol to about 5 to about 10 weight percent water-soluble alkali as potassium hydroxide to about 7 to about 15 weight percent water, as initially admixed components; i.e., components before reaction. The oleoresin and propylene glycol together constitute, at least about 75 weight percent of the saponification reaction mixture. More preferably, those weight ratios can be simply expressed as being about 4:4:1:1, in the order recited. In a particularly preferred embodiment, those weights are 41 percent oleoresin, 41 percent propylene glycol, and 18 percent aqueous potassium hydroxide (55 percent water). These ratios can vary depending on the plant material being used.

In addition, the saponification reaction preferably proceeds slowly. In an exemplary embodiment, about 1000 kg of marigold extract is mixed with the propylene glycol, which dissolves, or finely disperses the extract. The mixture is heated to a temperature range of about 50° to about 60° C., preferably about 55° C., to obtain a homogenous liquid having a viscosity similar to that of motor oil at room temperature. An aqueous potassium hydroxide solution is added slowly and evenly to the dissolved/dispersed extract (oleoresin) over a period of time to form the saponification reaction mixture. At least 10 minutes, but preferably 30 minutes are used for saponification reaction mixture formation with the above component amounts, and the mixture is maintained with gentle agitation for a period of time sufficient to saponify the xanthophyll diesters present, at least 3 hours, but preferably 10 hours.

When the alkali solution is initially added to the oleoresin, the temperature rises to about 70° C. and additional heat is added to maintain the temperature at about 65° C. to about 80° C., and preferably of about 70° C. during the entire reaction; i.e., until the saponification of the xanthophyll diester is complete. Completion of saponification can be readily determined as by a thin layer of chromatography (TLC) discussed hereinafter.

Sodium hydroxide can also be employed for the saponification, but the potassium soaps are more desirable because they are generally more soluble in aqueous solutions than are sodium soaps. The alkali used in the preferred embodiment of the invention is aqueous caustic potash that is 45 weight percent potassium hydroxide.

The saponification reaction cleaves the fatty acids from the xanthophyll diester, producing free xanthophyll in the form of crystals, as well as potassium or sodium soaps of the fatty acids. It is possible that propylene glycol mono-fatty acid esters are formed during the saponification. If present, those materials do not interfere with crystallization of the xanthophylls, possibly because of their greater water solubility as compared to mono-methyl or mono-ethyl esters of those fatty acids.

The saponification reaction mixture is then diluted by admixture with low ionic strength (deionized) water, preferably warm, e.g. about 60°–80° C., to further reduce the viscosity of the reaction mixture and to dissolve water-soluble impurities. If cold water is used, additional heat is provided to the diluted reaction mixture to maintain a temperature range of about 60° C. to about 80° C., preferably about 70° C.

If the temperature is too cold, the diluted reaction mixture is too viscous to filter. If the temperature is too hot, the diluted reaction mixture foams and interferes with crystal recovery.

Sufficient water is added to form a diluted reaction mixture that contains about 5 to about 25 volume percent of the saponification reaction mixture. Thus, about 3 to about 19 volumes of diluting water per reaction mixture volume are added. For a preferred embodiment, the ratio is about 10 volume percent saponification reaction mixture to about 90 volume percent diluting water.

The diluted reaction mixture formed by addition of water is gently agitated until homogeneous and then either pumped or otherwise fed into a filtration device that collects the crystals. Any filtration device known in the art can be used. In a preferred embodiment of the invention, the mixture is fed into a centrifuge/basket filter having a 35–40 μm maximum pore size.

The majority of the chemical impurities in the extract are removed during the filtration step due to the soluble nature of the formed fatty acid soaps themselves and their solubilizing power in a largely aqueous composition, and the insoluble nature of the xanthophyll crystals in that same aqueous composition. Other water-soluble impurities such as anthocyanins and water-soluble flavonoids are also removed.

After filtration, the collected crystals are washed extensively with low ionic strength (deionized) water at a temperature range of about 70° C. to about 90° C., preferably about 85° C. At the warm temperature employed, the water removes most of the residual chemical contaminants that may be present such as the potassium or sodium hydroxide, residual potassium soap and the propylene glycol used in the saponification reaction. The washed crystals are dried by a suitable methods such as freeze drying, rotary vacuum drying or by purging with heated nitrogen.

Based on UV/visible spectrophotometry, the resulting crystals obtained by this process contain approximately 70 to 85 percent total carotenoids, and are deemed substantially pure xanthophylls. In one embodiment of the invention in which lutein is isolated from marigold extract, the carotenoids, as determined by quantitative HPLC analysis, consist of 85 to 95 percent all-trans lutein, 0.2 to 1.5 percent of its geometrical isomers, 2.5 to 8.0 percent all-trans zeaxanthin, less than 1.0 percent of alpha- and beta-cryptoxanthin and traces of other carotenoids such as neoxanthin and violaxanthin. The presence of low levels of these other carotenoids is not of any concern because those other carotenoids are of dietary origin and are found routinely at much higher concentrations relative to that of lutein in human serum or plasma.

The lutein crystals contain approximately 0.5 to 5.0 percent water, and can contain traces of fatty acid soaps and/or fatty acids not completely washed from the crystals. However, the substantially pure xanthophyll obtained from this process does not contain residues of toxic organic solvents, (i.e., solvents other than propylene glycol) or other toxic compounds, and is suitable for human consumption.

The dried xanthophyll crystals so formed are typically admixed with an edible triglyceride oil for use in foods or as a cosmetic colorant. The xanthophyll content of the admixture is typically about 0.1 to about 35 percent by weight. Exemplary edible oils include candelilla, coconut, cod liver, cotton seed, menhaden, olive, palm, corn, soybean, peanut, poppy seed, safflower and sunflower oil. The use of an oil having a relatively high concentration of unsaturated fatty acids is preferred; i.e., the use of an oil having an iodine value of about 100–150 is preferred. The admixture is typically carried out using a high shear mixing apparatus, as is well known. Co-solvents and additives such as ethanol and α-tocopherol, respectively, can also be present as is noted in U.S. Pat. No. 5,382,714.

The following examples are offered to illustrate but not limit the present invention.

BEST MODE FOR CARRYING OUT THE INVENTION

EXAMPLE 1

Isolation of Lutein from Marigold Flower Petals

Extraction

Approximately 1000 kg of commercially available dried and ground marigold flower petals were pelleted and extracted with 40,000 liters of warm hexane (about 60° C.). The pellets were soaked for 1 hour and drained. This procedure was repeated 8 to 10 times to ensure complete extraction of the pigments present in the flowers. The hexane extracts were combined and the hexane was evaporated using vacuum and heat. After the hexane had been removed, approximately 100 kg of an oily extract (oleoresin) remained.

Saponification/crystallization reaction

Marigold oleoresin (1140 lbs—40.9 percent) was mixed with stirring with 1,2-propanediol (1140 lbs—40.9 percent) and heated to 55° C. to form a homogeneous stirable liquid. Aqueous caustic potash containing 45 weight percent potassium hydroxide (540 lbs—18.2 percent) was added slowly and evenly over a 30 minute period. The reaction temperature rose to 70° C. and was maintained at 70° C. for 10 hours with gentle agitation. Crystals of lutein appeared within this saponification reaction mixture during this time period.

Collection of lutein crystals

A portion of the saponified oleoresin (saponification reaction mixture; 232 lbs) produced from the above reaction was diluted to 10 percent with deionized water. This blend was heated to 70° C., agitated until homogeneous, and fed into a 30" TOLHURST™ centrifuge (available from Ketema Process Equipment, of Santee, Calif., equipped with a 35–40 μm maximum pore size filter. The collected lutein crystals were washed with deionized water (560 lbs) at 85° C. by spraying the warm water through nozzles onto the spinning wet cake. After washing, the wet crystals (28 lbs) were spread onto stainless steel trays and placed in a VIRTIS™ freeze dryer (available from Virtis Co., Gardiner, N.Y., and dried using the following drying conditions: frozen to –40° C., vacuum of 100 m torr drawn, heat supplied to the trays to 20° C., and a duration of 48 hours. Analysis of the crystals gave the following results:

| | |
|---|---|
| Crystal dry weight | 3.63 kg |
| Total carotenoid level (UV/visible spectrophotometry) | 79.0% |
| Lutein (HPLC adjusted*) | 73.6% |
| Moisture level (water) | 1.28% |

*93.1 percent of total carotenoid analyzed as all-trans lutein.

The recovery of carotenoids was 59 percent of the total carotenoids present in the starting oleoresin. The dried crystals were blended down with safflower oil using a high shear mixer. The final product of lutein in safflower oil contained 20 percent all-trans lutein.

Isolation and collection of capsanthin and capsorubin crystals

Similar manipulations using an oleoresin from dried red peppers of *Capsicum annum* in place of the ground marigold flower petal oleoresin provides a mixture of capsanthin and capsorubin crystals.

EXAMPLE 2

Isolation of Lutein from Marigold Flower Petals

Saponification/crystallization reaction

This study was performed using the same method as in Example 1 except that the reaction mixture contained 50.2 weight percent marigold oleoresin (1401 lbs) that was mixed with 30.4 weight percent 1,2-propanediol (848 lbs) and 19.4 weight percent aqueous potassium hydroxide (45 percent KOH; 542 lbs).

Also the saponified oleoresin (462 lbs) produced from the above reaction was diluted to 20.4 volume percent with deionized water and this diluted blend was fed into a 16" TOLHURST™ centrifuge equipped with a 25–30 μm maximum pore size filter and filtered. Analysis of the crystals showed a lower total carotenoid level, 64.7 percent than in Example 1.

EXAMPLE 3

Extraction, Isolation and Purification of Zeaxanthin from Wolfberries (*Lycium barbarum*)

Extraction

Seventy-five grams (75 g) of berries were hydrated and homogenized with 200 g water. Seeds were removed by filtration. The resulting material was centrifuged to form a carotenoid-containing pellet. Excess water was decanted. The pellet was spread and dried using heat and air. The dried material was ground fine and analyzed for total carotenoid content and was found to contain 6.46 g/kg.

A small portion of this material, 6 grams, was extracted with hexanes and ethyl acetate using 100 ml of each solvent with each 2 grams of dried fruit pellet. These extractions were conducted at 50° C. for several hours. The extracts were combined and filtered and then rotary evaporated under reduced pressure to apparent dryness to form an organic solvent-free oleoresin for saponification.

Saponification/crystallization

Approximately 1 g of dried oleoresin was suspended in 1 g of propylene glycol. To this mixture 0.5 g of 45 weight aqueous potassium hydroxide were added. This mixture was mixed with a small magnetic stir bar and heated to about 70° C. on a hot plate. Small aliquots were taken during the reaction and subjected to TLC analysis using silica gel and a 3:1 by volume mixture of hexane and acetone as eluting solvent for a qualitative measurement of the degree of saponification and for microscopic observations. TLC indicated a high degree of saponification after 3 hours. Microscopic observations showed formation of zeaxanthin crystalline structures over the course of the reaction.

The foregoing description and the examples are intended as illustrative and are not to be taken as limiting. Still other variations within the spirit and scope of this invention are possible and will readily present themselves to those skilled in the art.

We claim:

1. A process for producing xanthophyll crystals from a xanthophyll diester-containing plant oleoresin that comprises the steps of:

(a) admixing the oleoresin with propylene glycol with heating to a temperature of about 50° C. to about 60° C. to form a homogeneous liquid;

(b) admixing an aqueous alkali solution of sodium or potassium hydroxide with said homogeneous liquid to form a saponification reaction mixture that consists essentially of about 35 to about 50 weight percent oleoresin, about 30 to about 45 weight percent propylene glycol, about 5 to about 10 weight percent alkali as potassium hydroxide and about 7 to about 15 weight percent water as initially admixed components, wherein the total weight of said oleoresin plus propylene glycol constitute at least 75 weight percent of said reaction mixture;

(c) maintaining said saponification reaction mixture at a temperature of about 65° C. to about 80° C. for a time period sufficient to saponify the xanthophyll diester and form a saponified reaction mixture containing xanthophyll crystals;

(d) admixing about 3 to about 19 volumes of water at a temperature of about 60° C. to about 80° C. per volume of saponified reaction mixture to form a diluted reaction mixture containing xanthophyll crystals;

(e) gently admixing said diluted reaction mixture until homogeneous;

(f) collecting the xanthophyll crystals from said diluted reaction mixture; and (g) washing and then drying the collected xanthophyll crystals.

2. The process of claim 1 wherein the plant oleoresin is from marigold flowers (*Tagetes sp.*) and the xanthophyll is lutein.

3. The process of claim 1 wherein the plant oleoresin is from the fruit of wolfberry (*Lycium sp.*) and the xanthophyll is zeaxanthin.

4. The process of claim 1 wherein the ratio of oleoresin to alcohol to alkali to water is about 4:4:1:1 in the order recited.

5. The process of claim 1 wherein the alkali is potassium hydroxide.

6. The process of claim 1 wherein the saponification reaction mixture is maintained for a time period of at least 3 hours.

7. The process of claim 1 wherein the ratio of saponified reaction mixture to water is 1:9 by volume.

8. The process according to claim 1 including the further step of admixing said dried xanthophyll crystals with an edible triglyceride oil to form an admixture containing about 0.1 to about 35 weight percent xanthophyll.

* * * * *